United States Patent
Kuo et al.

(10) Patent No.: US 10,402,996 B2
(45) Date of Patent: Sep. 3, 2019

(54) DISTANCE MEASURING DEVICE FOR HUMAN BODY FEATURES AND METHOD THEREOF

(71) Applicant: ASUSTeK COMPUTER INC., Taipei (TW)

(72) Inventors: Hao-Yuan Kuo, Taipei (TW); Chia-Hui Han, Taipei (TW); Wei-Po Lin, Taipei (TW)

(73) Assignee: ASUSTEK COMPUTER INC., Taipei (TW)

( * ) Notice: Subject to any disclaimer, the term of this patent is extended or adjusted under 35 U.S.C. 154(b) by 216 days.

(21) Appl. No.: 15/705,347

(22) Filed: Sep. 15, 2017

(65) Prior Publication Data
US 2018/0089851 A1    Mar. 29, 2018

(30) Foreign Application Priority Data

Sep. 26, 2016    (CN) .......................... 2016 1 0849307

(51) Int. Cl.
*G06T 7/60* (2017.01)
*G01B 11/00* (2006.01)
(Continued)

(52) U.S. Cl.
CPC .................. *G06T 7/60* (2013.01); *A61B 3/00* (2013.01); *A61B 3/111* (2013.01); *A61B 5/00* (2013.01); *A61B 5/0077* (2013.01); *A61B 5/1072* (2013.01); *G01B 11/002* (2013.01); *G01B 11/14* (2013.01); *G01B 11/245* (2013.01); *G06T 7/593* (2017.01); *G06T 7/62* (2017.01); *G06T 2207/10028* (2013.01); *G06T 2207/10048* (2013.01); *G06T 2207/30196* (2013.01); *G06T 2207/30201* (2013.01); *H04N 5/33* (2013.01)

(58) Field of Classification Search
CPC .. G06T 7/60; G06T 7/593; G06T 7/62; G01B 11/14; G01B 11/002; G01B 11/245; A61B 3/00; A61B 5/00; A61B 5/0077; A61B 5/1072; A41H 1/02; G06K 9/00248
See application file for complete search history.

(56) References Cited

U.S. PATENT DOCUMENTS 9,600,993 B2 *    3/2017    Kimmel ............... G08B 21/043
9,974,466 B2 *    5/2018    Kimmel ............... A61B 5/1114
(Continued)

FOREIGN PATENT DOCUMENTS

CN           105708467 A      6/2016

*Primary Examiner* — David E Harvey
(74) *Attorney, Agent, or Firm* — McClure, Qualey & Rodack, LLP

(57) ABSTRACT

A distance measuring device for human body features is provided. The device comprises: an image capturing unit configured to capture a plurality of groups of human images of at least one part of human body in a time interval; an image processing unit configured to analyze to recognize a plurality of feature points in each group of the human images to generate three-dimensional coordinates for each feature point; and a processing unit configured to calculate a distance between a first feature point and a second feature point, calculate a deflection angle for each group of the human images, and generate a weight value. The processing unit has a weighted average calculation based on the weight values and the distances to generate a measurement result.

15 Claims, 8 Drawing Sheets

(51) Int. Cl.
*G01B 11/14* (2006.01)
*A61B 3/00* (2006.01)
*A61B 3/11* (2006.01)
*A61B 5/00* (2006.01)
*A61B 5/107* (2006.01)
*G01B 11/245* (2006.01)
*G06T 7/593* (2017.01)
*G06T 7/62* (2017.01)
*H04N 5/33* (2006.01)

(56) References Cited

U.S. PATENT DOCUMENTS

| | | | | |
|---|---|---|---|---|
| 10,013,756 B2* | 7/2018 | Kimmel | | G16H 40/67 |
| 2007/0201851 A1* | 8/2007 | Misawa | | G03B 13/18 |
| | | | | 396/125 |
| 2008/0050108 A1* | 2/2008 | Mizutani | | G02B 7/36 |
| | | | | 396/104 |
| 2008/0292151 A1* | 11/2008 | Kurtz | | A61B 3/10 |
| | | | | 382/128 |
| 2009/0022365 A1* | 1/2009 | Kotake | | G06K 9/32 |
| | | | | 382/103 |
| 2009/0273687 A1* | 11/2009 | Tsukizawa | | G06F 3/012 |
| | | | | 348/222.1 |
| 2012/0293643 A1* | 11/2012 | Hanna | | H04N 5/23212 |
| | | | | 348/78 |
| 2013/0070973 A1* | 3/2013 | Saito | | G06K 9/00228 |
| | | | | 382/118 |
| 2014/0168479 A1* | 6/2014 | Ishii | | H04N 5/23212 |
| | | | | 348/241 |
| 2014/0210964 A1* | 7/2014 | Muijs | | H04N 13/373 |
| | | | | 348/54 |
| 2014/0299775 A1* | 10/2014 | Kimmel | | G06K 9/00771 |
| | | | | 250/341.8 |
| 2014/0300907 A1* | 10/2014 | Kimmel | | A41H 1/02 |
| | | | | 356/625 |
| 2015/0003687 A1* | 1/2015 | Utsunomiya | | G06K 9/00348 |
| | | | | 382/107 |
| 2015/0015848 A1* | 1/2015 | Haddadi | | A61B 3/113 |
| | | | | 351/221 |
| 2015/0055085 A1* | 2/2015 | Fonte | | G06F 16/22 |
| | | | | 351/178 |
| 2015/0146169 A1 | 5/2015 | Ye et al. | | |
| 2015/0154453 A1* | 6/2015 | Wilf | | G06K 9/00711 |
| | | | | 382/103 |
| 2015/0206311 A1* | 7/2015 | Romanenko | | G06K 9/00248 |
| | | | | 382/228 |
| 2017/0112378 A1* | 4/2017 | Tamkin | | A61B 3/0025 |
| 2017/0147866 A1* | 5/2017 | Tokui | | G06T 7/73 |
| 2017/0155896 A1* | 6/2017 | Malaescu | | G02B 7/28 |
| 2018/0039745 A1* | 2/2018 | Chevalier | | G16H 10/60 |
| 2018/0121711 A1* | 5/2018 | Ge | | G06F 3/0484 |

* cited by examiner

DISTANCE MEASURING DEVICE FOR HUMAN BODY FEATURES AND METHOD THEREOF

CROSS-REFERENCE TO RELATED APPLICATION

This application claims the priority benefit of China application serial No. 201610849307.8, filed on Sep. 26, 2016. The entirety of the above-mentioned patent application is hereby incorporated by references herein and made a part of specification.

BACKGROUND OF THE INVENTION

Field of the Invention

The disclosure relates to a distance measuring device for human body features and a method thereof and, more specifically, to a distance measuring device for facial features and a method thereof.

Description of the Related Art

Generally, data required for customizing a clothing or an accessory in a store, such as a pupil distance, a height of eye position, a shoulder width, a body length, and a head circumference, should be manually measured, which is time-consuming.

BRIEF SUMMARY OF THE INVENTION

According to an aspect of the disclosure, a distance measuring device for human body features is provided. The distance measuring device for human body features comprises: an image capturing unit configured to capture a plurality of groups of human images with at least one part of human body in a time interval; an image processing unit configured to analyze each group of the human images to recognize a plurality of feature points in each group of the human images, and the image processing unit generates three-dimensional coordinates for each feature point; and a processing unit configured to calculate a distance between a first feature point and a second feature point of each group of the human images according to the three-dimensional coordinates of the first feature point and the second feature point in the feature points, calculate a deflection angle for each group of the human images according to the three-dimensional coordinate of each of the feature points, and generate a weight value corresponding to each distance according to the deflection angle, the processing unit is configured to have a weighted average calculation based on the weight values and the distances to generate a measurement result.

According to another aspect of the disclosure, a distance measuring method of human body features is provided. The distance measuring method of human body features comprises: capturing a plurality of groups of human images of at least one part of human body in a time interval; analyzing each group of the human images to recognize a plurality of feature points in the group of the human images; generating three-dimensional coordinates for each feature point; calculating a distance between a first feature point and a second feature point of each group of the human images according to the three-dimensional coordinates of the first feature point and the second feature point in the feature points; calculating a deflection angle for each group of the human images according to the three-dimensional coordinates of each of the feature points; generating a weight value corresponding to each distance according to the deflection angle; and having a weighted average calculation based on the weight values and the distances to generate a measurement result of the distance between the first feature point and the second feature point.

In embodiments, the distance between two feature points of the human body can be measured automatically by the distance measuring device for human body features. Compared with the manual measurement, the efficiency is improved and the measurement result is more precise by using the automatic measurement.

BRIEF DESCRIPTION OF THE DRAWINGS

These and other features, aspects and advantages of the disclosure will become better understood with regard to the following embodiments and accompanying drawings.

DETAILED DESCRIPTION OF THE EMBODIMENTS

Figure 1:
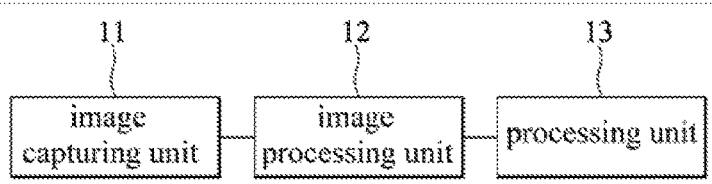
FIG. 1 is a block diagram showing a distance measuring device for human body features in an embodiment.
Figure 2:
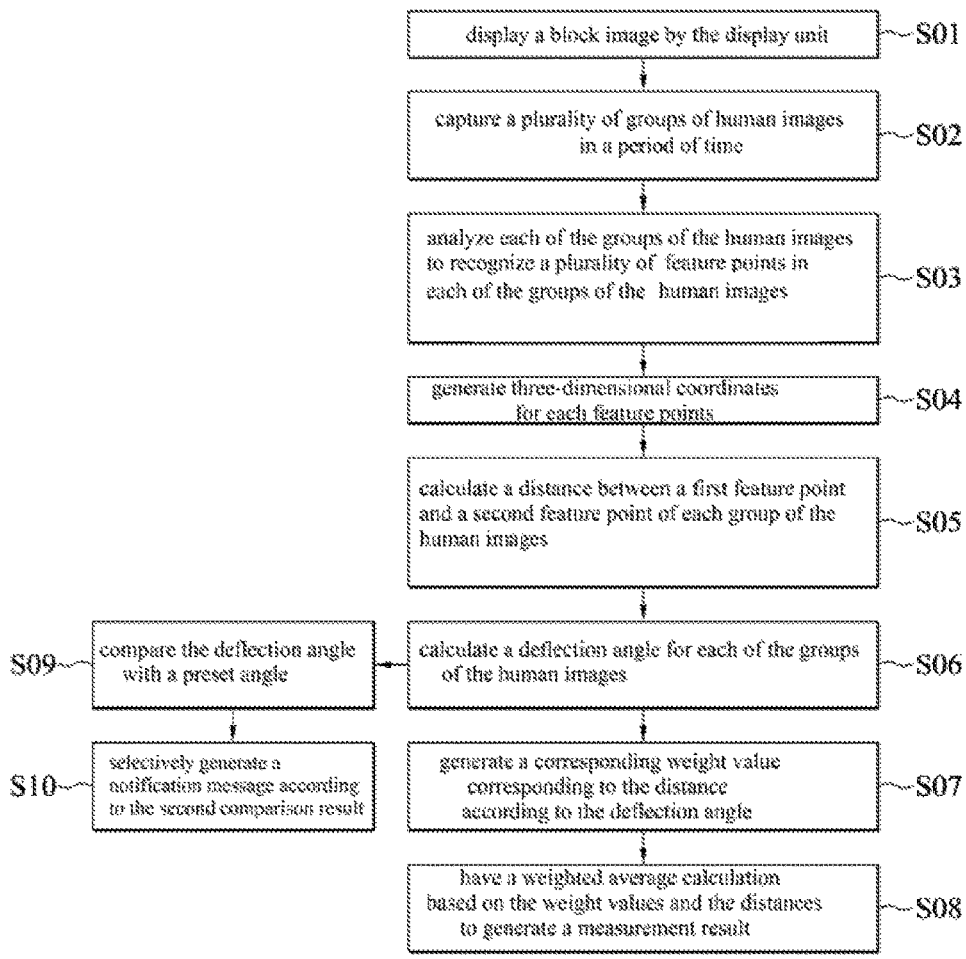
FIG. 2 is a flow chart of a distance measuring method for human body features in an embodiment.
Figure 3:
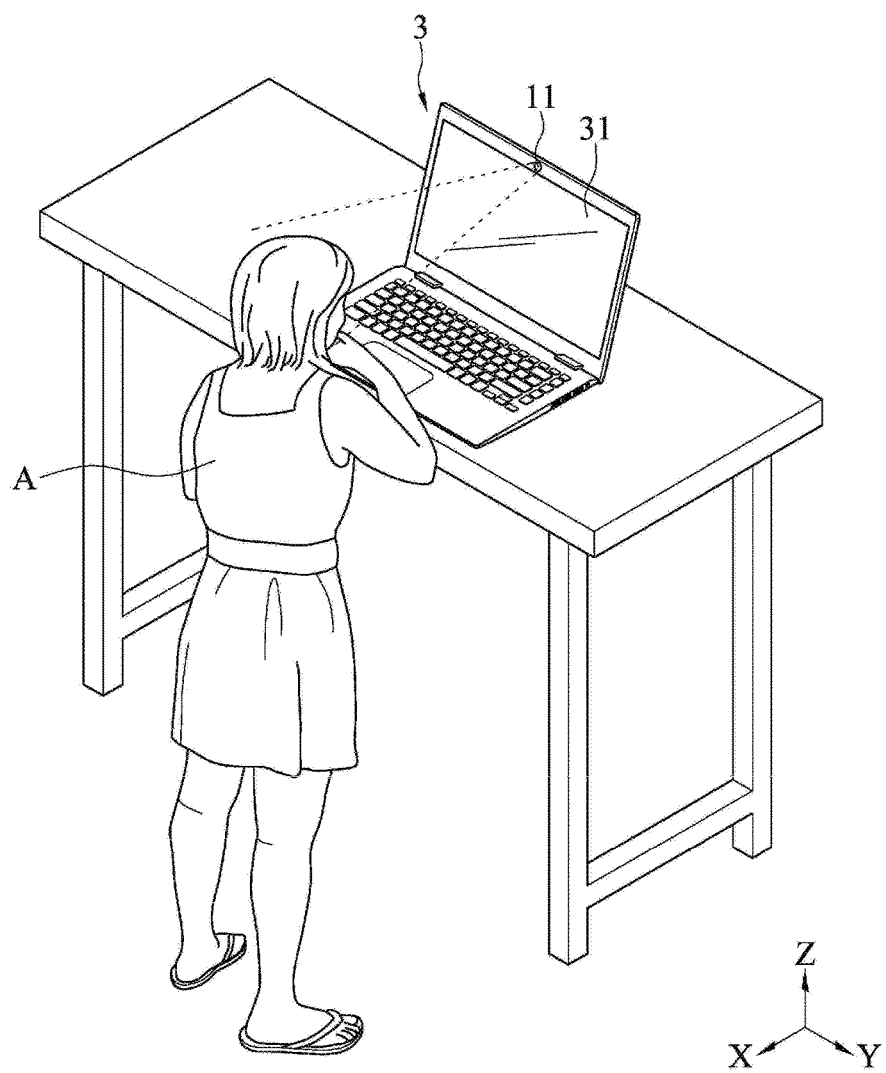
FIG. 3 is a schematic diagram showing that the distance measuring device for human body features in FIG. 1 is applied to a tester in an embodiment.
Figure 4:
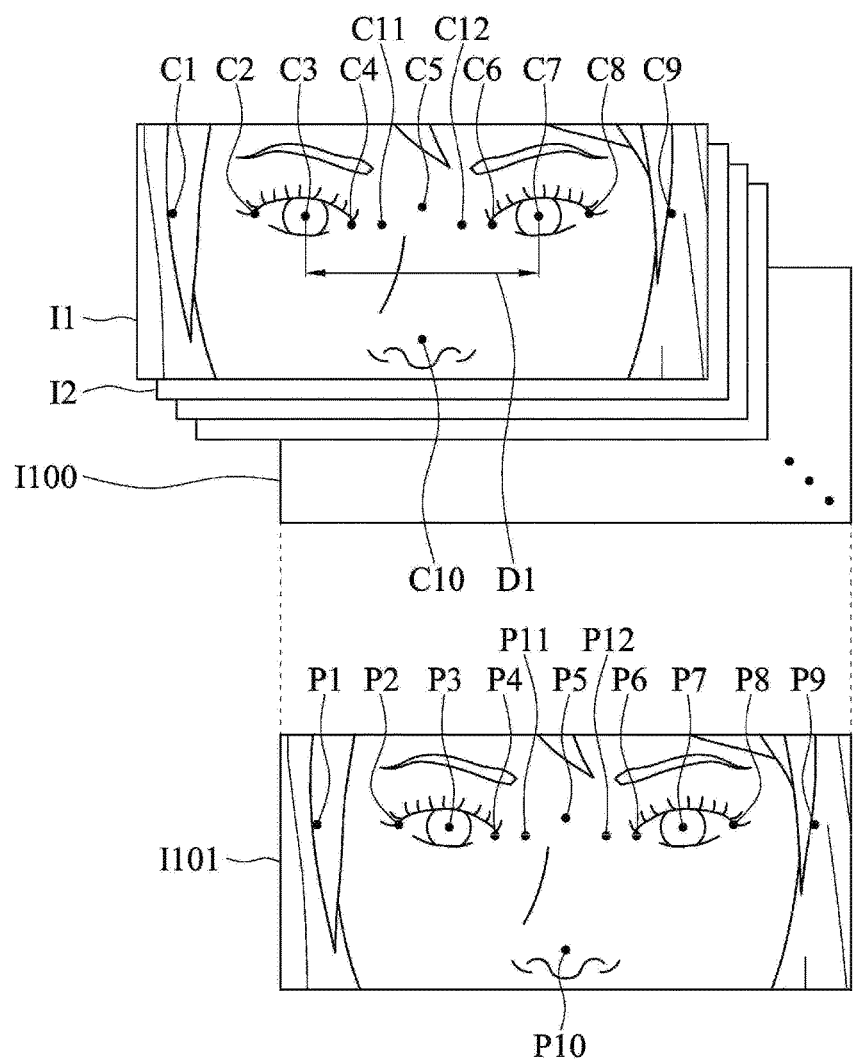
FIG. 4 is a schematic diagram showing groups of the human images (each includes a human face) and a sample group of human images in an embodiment.

FIG. 1 is a block diagram showing a distance measuring device for human body features in an embodiment. FIG. 2 is a flow chart of a distance measuring method for human body features in an embodiment. FIG. 3 is a schematic diagram showing that the distance measuring device for human body features in FIG. 1 is applied to a tester A in an embodiment. FIG. 4 is a schematic diagram showing groups I1-I100 of the human images (each includes a human face) and a sample group of the human images I101 in an embodiment. Please refer to FIG. 1 and FIG. 4. As shown in FIG. 1, a distance measuring device for human body features includes an image capturing unit 11, an image processing unit 12 and a processing unit 13. The distance measuring device for human body features measures a linear distance between two feature points of the human body. As shown in FIG. 3, the distance measuring device for human body features shown in FIG. 1 is combined with an electronic device 3. In an embodiment, the electronic device 3 is a computer, a tablet computer, a smartphone or a personal digital assistant (PDA), which is not limited herein. The image capturing unit 11 is configured at a housing of the electronic device 3. The image processing unit 12 and the processing unit 13 are central processing units (CPU), microcontrollers (MCU) or application-specific integrated circuits (ASIC). In an embodiment, the image processing unit 12 and the processing unit 13 are configured inside the electronic device 3.

In the embodiment, a tester A is tested in front of the image capturing unit 11. The image capturing unit 11 of the distance measuring device of human body features is configured to capture a plurality of groups of human images of at least one part of the tester A's body in a time interval (step S02). In an embodiment, the at least one part of the body is a human face. For example, the image capturing unit 11 successively captures one hundred groups I1-I100 of the human images with the face of the tester A at different time points in three seconds, as shown in FIG. 4. The image processing unit 12 is coupled between the image capturing unit 11 and the processing unit 13. The image processing unit 12 receives the groups of the human images I1-I100 and performs an image analysis. The image processing unit 12 analyzes each of the groups of the human images to recognize a plurality of feature points (such as twelve feature points C1-C12) in each of the groups of the human images I1-I100 (step S03). The image processing unit 12 generates three-dimensional coordinates for the twelve feature points C1-C12 of each of the groups of the human images I1-I100 (step S04). The three-dimensional coordinate includes an X-axis, a Y-axis and a Z-axis Cartesian coordinates.

Then, the processing unit 13 receives the three-dimensional coordinates of the feature points C1-C12 of each of the groups of the human images from the image processing unit 12. The processing unit 13 calculates a distance between the two feature points (such as, a first feature point and a second feature point) according to the three-dimensional coordinates of the two of the feature points C1-C12 of each of the groups of the human images (step S05). For example, the first feature point and the second feature point are feature points C3 and C7, respectively. The processing unit 13 calculates the linear distance between the feature point C3 and the feature point C7 in each of the groups of the human images to generate one hundred groups of distances D1-D100.

In an embodiment, when the tester A's face does not directly face to the image capturing unit 11 or the tester A's face slightly moves or turns around in testing, the distances D1-D100 calculated by the processing unit 13 according to the groups of the human images I1-I100 are affected by different deflection angles of the tester's face. Therefore, the processing unit 13 calculates the deflection angle for each of the groups of the human images I1-I100 according to the three-dimensional coordinates of the feature points C1-C12 (step S06). In the embodiment, totally one hundred groups of the facial deflection angles are calculated for the groups of the human images I1-I100. Then, the processing unit 13 generates corresponding weight values corresponding to the distances D1-D100 respectively according to the one hundred groups of the deflection angles (step S07). Each deflection angle is negatively correlated to the corresponding weight value. That is, the weight value decreases as the deflection angle increases, and the weight value increases as the deflection angle decreases. Then, the processing unit 13 has a weighted average calculation based on the one hundred groups of the weight values and the one hundred groups of the distances to generate a measurement result (step S08). The measurement result is a weighted average of the one hundred groups of the distances D1-D100. That is, the importance degree of the distances corresponding to smaller deflection angles in the distances D1-D100 is raised and the importance degree of the distances corresponding to larger deflection angles in the distances D1-D100 is reduced. As a result, errors between the measurement result and the actual distances are reduced. In an embodiment, the electronic device 3 includes a display unit 31. The display unit 31 is coupled to the processing unit 13. The processing unit 13 converts the weighted average of the distances D1-D100 into an image signal and sends the image signal to the display unit 31 to allow the tester to know the measurement result of the distance between the two feature points via a display screen of the display unit 31.

In an embodiment, the number of the groups of the human images (that are detected by the distance measuring device for human body features) and the number of the feature points (that are detected by the distance measuring device for human body features) is reduced or increased according to requirements. For example, the number of the groups of the human images is fifty, and the number of the feature points is sixty-four. In the embodiment, the processing unit 13 totally generates 50 groups of the distances, 50 groups of the weight values, 50 groups of the deflection angles and 3200 groups of the three-dimensional coordinates.

In an embodiment, in step S05, the processing unit 13 calculates the linear distance between the first feature point and the second feature point to obtain the distance between the first feature point and the second feature point. In an embodiment, for Cartesian coordinates, it is assumed that the image processing unit 12 generates the three-dimensional coordinates $(X_i, Y_i, Z_i)$ and $(X_i', Y_i', Z_i')$ for the first feature point and the second feature point of the $i^{th}$ group of the human images. The processing unit 13 calculates the distance $D_i$ for the $i^{th}$ group of the human images in the groups of the human images I1-I100 according to a formula 1, wherein i ranges from 1 to 100.

$$D_i \sqrt{(X_i-X_i')^2+(Y_i-Y_i')^2+(Z_i-Z_i')^2} \quad \text{formula 1}$$

Additionally, it is assumed that the $i^{th}$ group of the human images has a deflection angle $\theta_i$. For Cartesian coordinates, each deflection angle $\theta_i$ refers to a sum of the angle (called as a first angle) between the tester's face and the X axis, the angle (called as a second angle) between the face and the Y axis, and the angle (called as a third angle) between the face and the Z axis. When the first angle, the second angle and the third angle are 2 degrees, 3 degrees and 5 degrees, respectively, the deflection angle $\theta_i$ is 10 degrees. The processing unit 13 calculates the sum of the first angle, the second angle and the third angle to obtain the deflection angle $\theta_i$. When step S07 is performed, the processing unit 13 generates the weight value $w^i$ corresponding to the distance $D_i$ according to a formula 2:

$$w_i = 1 - \frac{1}{1+e^{-2\times(|\theta_i|-c)}} \quad \text{formula 2}$$

wherein c represents a constant.

In the embodiment, it can be seen from the formula 2, the weight value $w_i$ ranges from 0 to 1. When the deflection angle $\theta_i$ increases, the weight value $w_i$ approaches to zero.

When the deflection angle $\theta_i$ decreases, the weight value $w_i$ approaches to 1. Then, the processing unit 13 calculates the weighted averages (i.e., the measurement results of the two feature points) of the one hundred groups of the distances D1-D100 based on the distances $D_i$ and the corresponding weight value $w_i$ of each group of the human images to be measured via a formula 3.

$$\frac{\sum_{i=100}^{i=1} D_i \times w_i}{\sum_{i=100}^{i=1} w_i} \quad \text{formula 3}$$

In an embodiment, in step S06, the processing unit 13 generates the deflection angle for each group of the human images according to the three-dimensional coordinates of multiple feature points (that is, sample feature points P1-P12) of the sample group of the human images I101 and the three-dimensional coordinates of the feature points C1-C12. The sample group of the human images I101 refers to a group of the facial images with no facial deflection. That is, the deflection angle for the sample group of the human images I101 is zero degree. The sample feature points P1-P12 and the feature points C1-C12 correspond to the same facial features, respectively. In an embodiment, the three-dimensional coordinates of the sample feature points P1-P12 are taken as reference values. The processing unit 13 calculates the deflection angle $\theta_i$ for each face in the groups of the human images I1-I100, according to a displacement relationship, a size relationship or a deflection relationship between the three-dimensional coordinates of the feature points C1-C12 and the three-dimensional coordinates of the sample feature points P1-P12. In an embodiment, the three-dimensional coordinates of the sample feature points P1-P12 are pre-stored in a storage of the processing unit 13 or other storage units before the tester A is tested.

Figure 5:
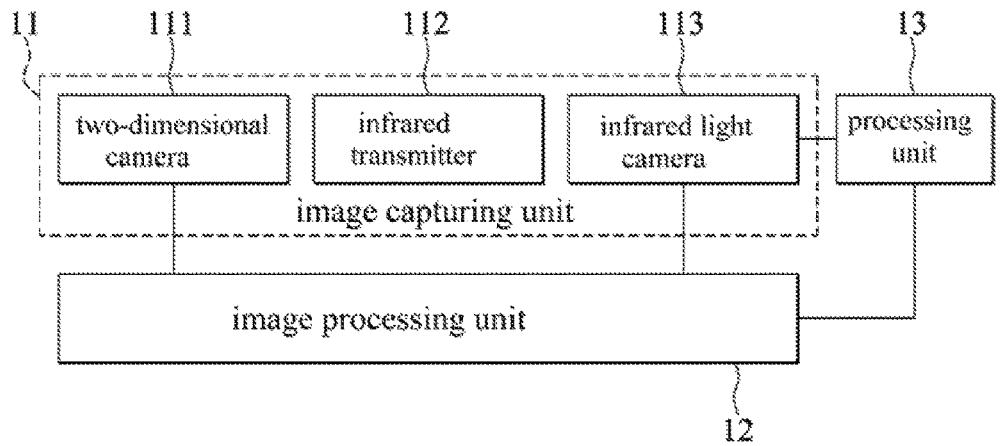
FIG. 5 is a block diagram showing an image capturing unit in FIG. 1 in an embodiment.
Figure 6:
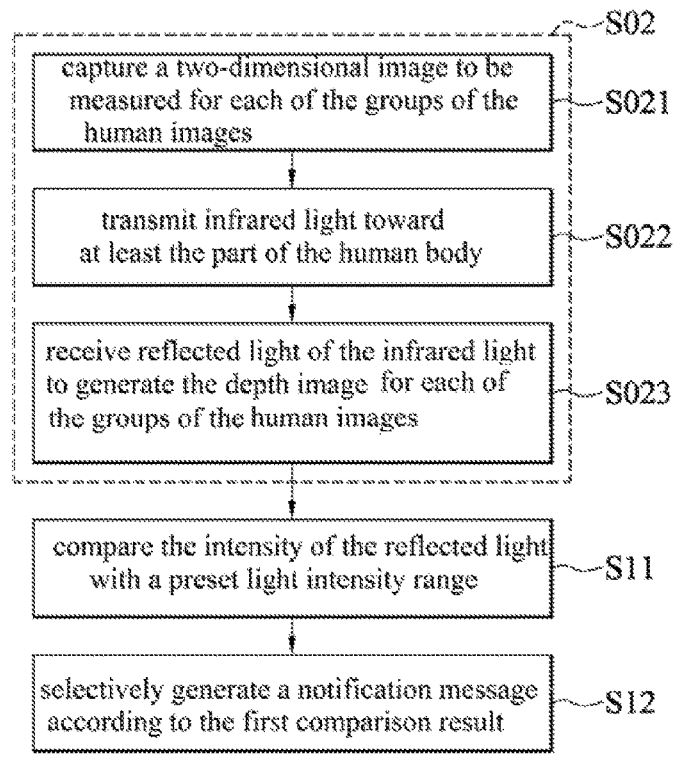
FIG. 6 is a flow chart of the distance measuring method for human body features in FIG. 2 in an embodiment.
Figure 7:
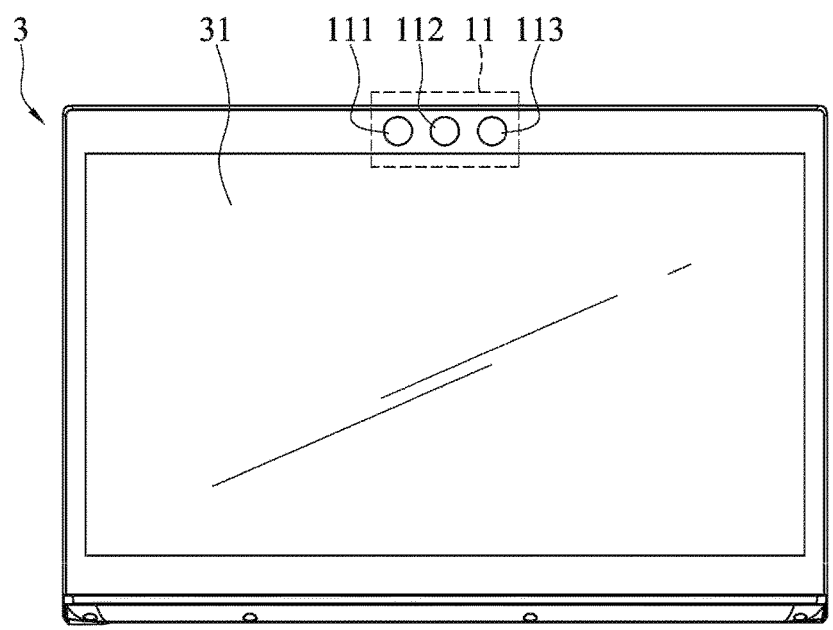
FIG. 7 is a schematic diagram showing an appearance of an electronic device combined with the image capturing unit in FIG. 5 in an embodiment.

FIG. 5 is a block diagram showing the image capturing unit 11 in FIG. 1 in an embodiment. FIG. 6 is a flow chart of the distance measuring method for human body features in FIG. 2 in an embodiment. FIG. 7 is a schematic diagram showing an appearance of the electronic device 3 combined with the image capturing unit 11 in FIG. 5 in an embodiment. In an embodiment, each of the groups of the human images I1-I100 includes a two-dimensional image and a depth image. In step S02, the image capturing unit 11 captures the two-dimensional image and the depth image of at least one part of the human body. Please refer to FIG. 5 to FIG. 7. The image capturing unit 11 includes a two-dimensional camera 111, an infrared emitter 112 and an infrared light camera 113. In an embodiment, the two-dimensional camera 111, the infrared emitter 112 and the infrared light camera 113 are integrated to the electronic device 3. The two-dimensional camera 111 is configured to capture the two-dimensional image (step S021). Each two-dimensional image includes two-dimensional coordinates of the feature points C1-C12. The infrared emitter 112 and the infrared light camera 113 is configured to capture the depth images. Each depth image includes depth information of the feature points C1-C12. That is, in an embodiment, the infrared emitter 112 emits infrared light toward the at least one part of the human body (such as the face) of the tester A (step S022). The infrared light reaches the tester's face and is reflected from the tester's face. The infrared light camera 113 includes a CMOS infrared light sensor. The infrared light camera 113 receives the reflected light of the infrared light (which is reflected by the tester's face) to generate the depth image (step S023). The infrared light camera 113 generates the depth information according to a product of the speed of light multiplied by a time difference between the emission of the infrared light and the arrival of the reflected light. In an embodiment, the two-dimensional camera 111 is a color camera or a grayscale camera. The two-dimensional image captured by the two-dimensional camera 111 is a color image (such as a RGB image) or a grayscale image.

The image processing unit 12 is coupled to the two-dimensional camera 111 and the infrared light camera 113 to receive the two-dimensional image and the depth image. When step S04 is performed, the image processing unit 12 performs an image processing process to generate the three-dimensional coordinates of the feature points C1-C12 for each group of the images I1-I100 by performing mapping and projection conversion based on the two-dimensional coordinates and the depth information of the feature points C1-C12.

In the embodiment, as show in FIG. 5, the processing unit 13 is coupled to the infrared light camera 113 to receive each of depth information. The processing unit 13 obtains the intensity of the reflected light according to the depth information. The processing unit 13 determines whether the distance between the tester A and the image capturing unit 11 is in a proper range via the intensity of the reflected light. When the distance between the tester A and the image capturing unit 11 is too long or too short, the distances D1-D100 calculated by the processing unit 13 is not useful. In the embodiment, after the step S02, the processing unit 13 compares the intensity of the reflected light with a preset light intensity range (step S11) to generate a first comparison result. The processing unit 13 selectively generates a notification message according to the first comparison result (step S12). In an embodiment, the preset light intensity range is defined as a sum of the intensities of the reflected light received by the infrared light camera 113 when the tester A is located at different positions in the proper range of the distance between the tester A and the image capturing unit 11. When the first comparison result indicates that the intensity of the reflected light is in the preset light intensity range, the processing unit 13 determines that the tester A is in the proper range of the distance between the tester A and the image capturing unit 11. When the first comparison result indicates that the intensity of the reflected light is out of the preset light intensity range, the processing unit 13 determines that the distance between the tester A and the image capturing unit 11 is too far or too close to the preset light intensity range, and generates the notification message. The notification message is one or a combination of a text, an image and a voice, which is used to notify the tester A to adjust the position until the notification message disappears. In an embodiment, the proper range of the distance between the tester A and the image capturing unit 11 is from 30 cm to 50 cm.

Figure 8:
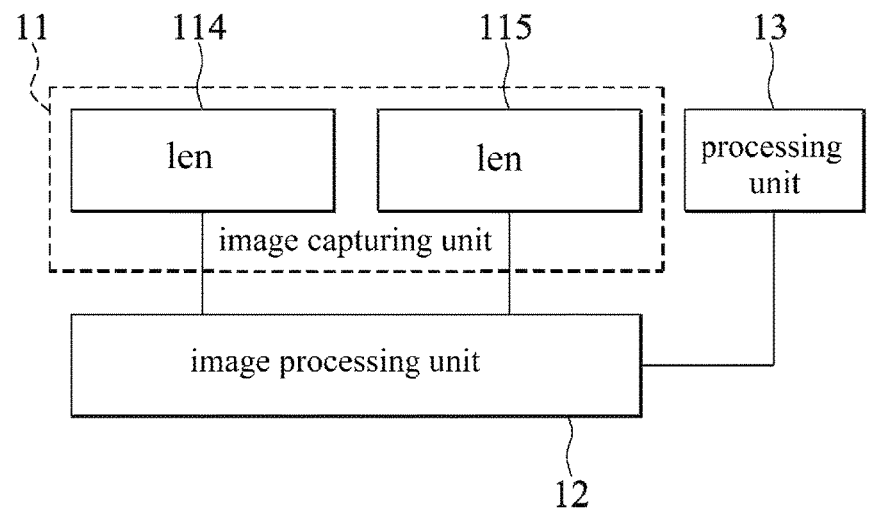
FIG. 8 is a block diagram showing an image capturing unit in FIG. 1 in an embodiment.
Figure 9:
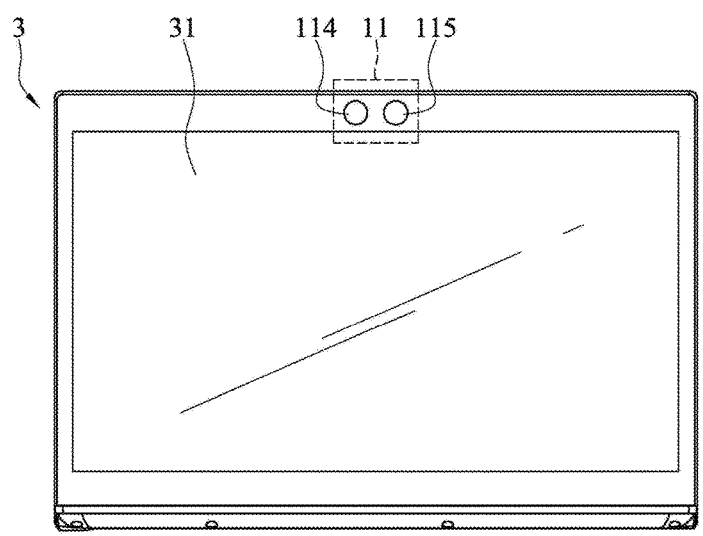
FIG. 9 is a schematic diagram showing an appearance of an electronic device combined with the image capturing unit in FIG. 8 in an embodiment.

FIG. 8 is a block diagram showing the image capturing unit 11 in FIG. 1 in an embodiment. FIG. 9 is a schematic diagram showing an appearance of the electronic device 3 combined with the image capturing unit 11 in FIG. 8 in an embodiment. In an embodiment, each group of the images I1-I100 includes a first image (in the embodiment, the first image is a left image) and a second image (in the embodiment, the second image is a right image). The image capturing unit 11 captures the left image and the right image of the tester's face. Please refer to FIG. 8 and FIG. 9. The image capturing unit 11 is a dual-camera device. That is, the image capturing unit 11 includes two lens 114 and 115. In an embodiment, the two lens 114 and 115 are combined to the housing of the electronic device 3. The two lens 114 and 115 are located in a same horizontal plane and spaced from each other by a distance. The two lens 114 and 115 have the same focal distances. When step S02 is performed, the two lens 114 and 115 synchronously capture the color image or the grayscale image of the tester's face at a same time point or in the same time interval to generate a group of two-dimensional human images (for example, the groups of the human images generated by the lens 114 is the left images, the groups of the human images generated by the lens 115 is the right images). The image processing unit 12 is coupled to the two lens 114 and 115 to receive each left image and each right image. When step S04 is performed, the image processing unit 12 performs an image processing process. The image processing unit 12 calculates a pixel-value difference between the left image and the right image. The image processing unit 12 calculates the depth information of the feature points C1-C12 of each group of the images I1-I100 by using the similar triangular principle according to the distance between the two lens 114 and 115, the focal distance and the pixel-value difference, to generate the three-dimensional coordinates of the feature points C1-C12 of each group of the images I1-I100.

In an embodiment, the processing unit 13 determines whether the deflection angle $\theta_i$ for each group of the human images is smaller than a preset angle. When the deflection angle $\theta_i$ is smaller than or equal to the preset angle, that means the error between the measurement result and the actual distance is less than or equal to a tolerable error. When the deflection angle $\theta_i$ is greater than the preset angle, that means the error is larger than the tolerable error. In the embodiment, when step S06 is performed, the processing unit 13 compares each deflection angle $\theta_i$ with the preset angle (step S09) to generate a second comparison result. The processing unit 13 selectively generates the notification message according to the second comparison result (step S10). That is, when any one of the deflection angles $\theta_i$ in the groups of the human images I1-I100 is equal to or smaller than the preset angle, the processing unit 13 does not generate the notification message. When any one of the deflection angles $\theta_i$ in the groups of the human images I1-I100 is greater than the preset angle, the processing unit 13 sends the notification message to notify the tester A to adjust the deflection angle between the face and the image capturing unit 11 until the notification message disappears. In an embodiment, the preset angle is 15 degrees. That is, the sum of the first angle, the second angle and the third angle is 15 degrees.

Figure 10:
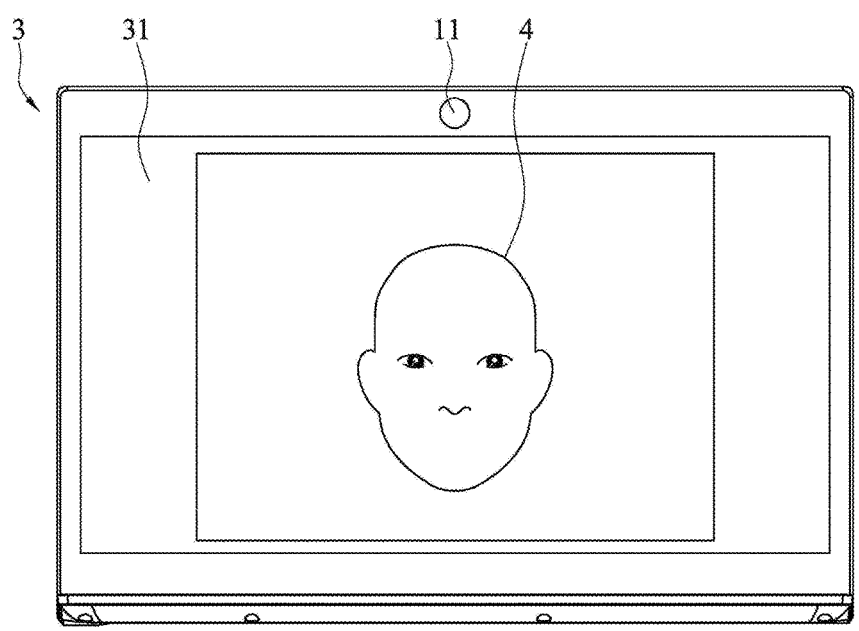
FIG. 10 is a schematic diagram showing a block image displayed by a display unit in FIG. 3 in an embodiment.

FIG. 10 is a schematic diagram showing a block image 4 displayed by a display unit in FIG. 3 in an embodiment. In an embodiment, as shown in FIG. 10, a block image 4 is displayed by the display unit 31 (step S01) before performing step S02. The size of the block image 4 (an area enclosed by the boundary of the block image 4) is positively correlated to the preset light intensity range. That is, the processing unit 13 generates an image signal corresponding to the preset light intensity range to make the display unit 31 display the block image. The size of the block image 4 increases as the preset light intensity range increases. The size of the block image 4 decreases as the preset light intensity range decreases. The size of the block image 4 is positively correlated to the preset light intensity range. In an embodiment, the block image 4 includes a plurality of patterns of facial features, such as eye and nose patterns. In the embodiment, the tester A adjusts the distance between himself/herself and the image capturing unit 11 and the deflection angle of the face via the block image 4. When the tester's face image is located within the boundary of the block image 4 and the positions of his/her facial features conform to the positions of the facial feature patterns in the block image 4, that means the current distance between the tester A and the image capturing unit 11 is in the proper range (that is, in the range of 30 cm to 50 cm), and the deflection angle of the tester's face is smaller than or equal to the preset angle (15 degrees). At the time, the error value of the weighted average output from the processing unit 13 is within 2 mm.

Figure 11A:
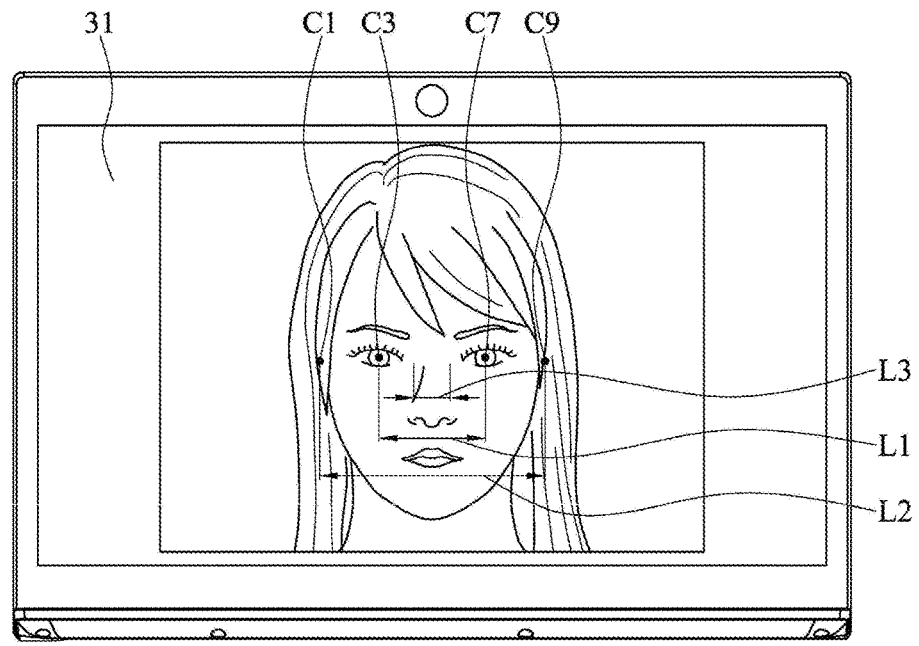
FIG. 11A is schematic diagram showing distances between different feature points (which are displayed by a display unit in FIG. 3) in an embodiment.
Figure 11B:
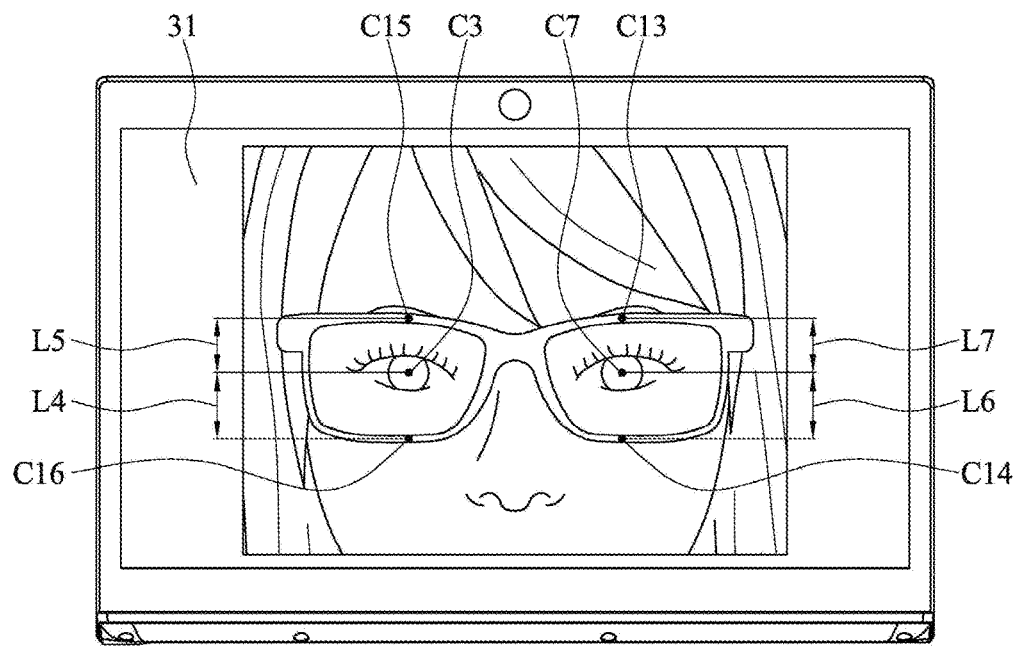
FIG. 11B is a schematic diagram showing distances between different feature points (which are displayed by a display unit in FIG. 3) in an embodiment.

FIG. 11A and FIG. 11B are diagrams showing distances between different feature points (which are displayed by the display unit in FIG. 3) in an embodiment. Please refer to FIG. 11A. The feature points C3 and the feature points C7 are right and the left pupils of the tester A. When the first feature point and the second feature point are the feature points C3 and the feature points C7, respectively, the measurement result generated by the processing unit 13 is a pupil distance L1 of the tester A. When the two different feature points are selected from the feature points C1-C12, such as, the feature points C1 and C9 or the feature points C12 and C11, the processing unit 13 calculates a facial width L2 and a width L3 of the bridge of the nose of the tester, respectively.

In an embodiment, as shown in FIG. 11B, when the tester A with a pair of eyeglasses is tested, the groups of the human images I1-I100 include images with the eyeglasses. The image processing unit 12 further recognizes the upper edges (the feature points C13 and C15) of the eyeglass frame above the pupil, and bottom edges (the feature points C14 and C16) of the eyeglass frame below the pupil. In the embodiment, when the first feature point is the feature point C3 and the second feature point is the feature point C15 or C16, the processing unit 13 calculates a height L5 of the tester A's upper eye distance and a height L4 of the tester A's lower eye distance. When the first feature point is the feature point C7, the second feature point is the feature point C13 or C14. At the time, the processing unit 13 calculates a height L7 of the upper eye distance of the tester A's left eye and a height L6 of the lower eye distance of the tester A's left eye.

In sum, a suitable eyeglass frame is selected by the tester according to facial feature information, such as the facial width and the width of the bridge of nose. For example, the eyeglass frame with a smaller width is selected by the tester with a small facial width. In an embodiment, with the disclosure of the invention, when a pair of eyeglasses is customized, the pupil distance of the tester is detected and glasses suitable for the tester is made. Bifocal glasses can be made according to the height of the eye positon of the tester. The measurement error is reduced to be within 2 mm, which further reduces the cost.

In an embodiment, the distance measuring device for human body features further includes a storage unit for storing information of the eyeglass frame, such as a color and a style of the eyeglass frame. The processing unit 13 is configured to obtain the information of the eyeglass frame that is suitable for the tester from a database according to the facial information, and combine the information of the eyeglass frame with the facial image. Then, and display a plurality of virtual images are displayed by the display unit 31 for the user to choose.

In an embodiment of the distance measuring device for human body features, the image capturing unit captures the groups of the human images via infrared light. Compared with laser light, the infrared light has less damage to the human body. By using the infrared light, the measurement is more efficient and the measurement result is more precise.

Although the disclosure has been disclosed with reference to certain embodiments thereof, the disclosure is not for limiting the scope. Persons having ordinary skill in the art may make various modifications and changes without departing from the scope of the disclosure. Therefore, the scope of the appended claims should not be limited to the description of the embodiments described above.

What is claimed is:

1. A distance measuring device for human body features, comprising:
    an image capturing unit configured to capture a plurality of groups of human images with at least one part of human body in a time interval;
    an image processing unit configured to analyze each group of the human images and recognize a plurality of feature points in each group of the human images, the image processing unit generates three-dimensional coordinates for each feature point; and
    a processing unit configured to calculate a distance between a first feature point and a second feature point of each group of the human images according to the three-dimensional coordinates of the first feature point and the second feature point in the feature points, calculate a deflection angle for each group of the human images according to the three-dimensional coordinate of each of the feature points, and generate a weight value corresponding to each distance according to the deflection angle, the processing unit is configured to have a weighted average calculation based on the weight values and the distances to generate a measurement result.

2. The distance measuring device for human body features according to claim 1, wherein the processing unit is configured to generate the deflection angle according to the three-dimensional coordinates of each of the feature points and three-dimensional coordinates of a sample feature point corresponding to each of the feature points.

3. The distance measuring device for human body features according to claim 1, wherein the $i^{th}$ group of the human image in the groups of the human images has the deflection angle $\theta_i$, and the processing unit generates the weight value $w_i$ corresponding to the deflection angle $\theta_i$ according to an equation as follow:

$$w_i = 1 - \frac{1}{1 + e^{-2 \times (|\theta_i| - c)}}$$

wherein c represents a constant.

4. The distance measuring device for human body features according to claim 1, wherein each group of the human images includes a two-dimensional image and a depth image.

5. The distance measuring device for human body features according to claim 4, wherein the image capturing unit includes:
    a two-dimensional camera for generating the two-dimensional image, the two-dimensional image includes two-dimensional coordinates for each of the feature points;
    an infrared emitter for emitting infrared light toward the at least one part of the human body; and
    an infrared light camera for receiving reflected light of the infrared light, the infrared light camera generates the depth image according to the reflected light, and the depth image includes depth information of each of the feature points;
    wherein the image processing unit generates the three-dimensional coordinates for each of the feature points by performing mapping and projection conversion based on the two-dimensional coordinates and the depth information.

6. The distance measuring device for human body features according to claim 5, wherein the processing unit obtains an intensity of the reflected light according to the depth information, the processing unit compares the intensity of the reflected light with a preset light intensity range, the processing unit generates a notification message when the intensity of the reflected light is out of the preset light intensity range.

7. The distance measuring device for human body features according to claim 1, wherein the image capturing unit includes two lens for capturing the group of the human images at a same time point in the time interval, the group of the human images to be measured includes a first image and a second image; the image processing unit calculates a pixel-value difference between the first image and the second image, and generates the three-dimensional coordinates for each of the feature points according to a distance between the two lens, focal distances of the two lens and the pixel-value difference.

8. The distance measuring device for human body features according to claim 1, wherein the deflection angle is a sum of angles between the at least one part of human body of each of the groups of the human images and an X axis, a Y axis and a Z axis respectively, the processing unit compares the deflection angle with a preset angle, and sends a notification message when the deflection angle is greater than the preset angle.

9. A distance measuring method of human body features, comprising:
    capturing a plurality of groups of human images with at least one part of human body in a time interval;
    analyzing each group of the human images to recognize a plurality of feature points in the group of the human images;
    generating three-dimensional coordinates for each feature point;
    calculating a distance between a first feature point and a second feature point of each group of the human images according to the three-dimensional coordinates of the first feature point and the second feature point in the feature points;
    calculating a deflection angle for each group of the human images according to the three-dimensional coordinates of each of the feature points;
    generating a weight value corresponding to each of the distance according to the deflection angle; and
    having a weighted average calculation based on the weight values and the distances to generate a measurement result of the distance between the first feature point and the second feature point.

10. The distance measuring method of the human body features according to claim 9, wherein the step of calculating the deflection angle for each group of the human images according to the three-dimensional coordinates of each of the feature points includes generating the deflection angle according to the three-dimensional coordinates of each of the feature points and three-dimensional coordinates of a sample feature point.

11. The distance measuring method of the human body features according to claim 9, wherein the step of generating the weight value includes the weight value $w_i$ corresponding to each distance is generated according to a following equation with the deflection angle $\theta_i$:

$$w_i = 1 - \frac{1}{1+e^{-2\times(|\theta_i|-c)}}$$

wherein c represents a constant.

12. The distance measuring method of the human body features according to claim 9, wherein the step of capturing the groups of the human images with the at least one part of the human body in the time interval includes:
  obtaining a two-dimensional image of each group of the human images, the two-dimensional image includes two-dimensional coordinates for each of the feature points;
  emitting infrared light toward the at least one part of the human body; and
  receiving reflected light of the infrared light to generate a depth image according to the reflected light, the depth image includes depth information of each of the feature points;
  wherein the step of generating the three-dimensional coordinates for each feature point includes generating the three-dimensional coordinates for each of the feature points by performing mapping and projection conversion based on the two-dimensional coordinates and the depth information.

13. The distance measuring method of the human body features according to claim 12, wherein after the step of capturing the groups of human images with the at least one part of the human body in the time interval, the distance measuring method of the human body features further includes:
  comparing an intensity of the reflected light with a preset light intensity range to generate a first comparison result; and
  selectively generating a notification message according to the first comparison result.

14. The distance measuring method of the human body features according to claim 9, wherein the step of capturing the groups of human images with at least the part of the human body in the time interval includes capturing a first image and a second image of the group of the human images via two lens, the two lens have same focal distances and a distance therebetween, and the step of generating the three-dimensional coordinates for each feature point includes:
  calculating a pixel-value difference between the first image and the second image, and
  generating the three-dimensional coordinates for each of the feature points according to the distance, the focal distances and the pixel-value difference.

15. The distance measuring method of the human body features according to claim 9, wherein after the step of calculating the deflection angle for each group of the human images according to the three-dimensional coordinates of each of the feature points, the distance measuring method of the human body features further includes:
  comparing the deflection angle with a preset angle to generate a second comparision result; and
  selectively generating a notification message according to the second comparision result.

* * * * *